United States Patent
Brauer et al.

(10) Patent No.: US 10,557,802 B2
(45) Date of Patent: Feb. 11, 2020

(54) CAPTURE OF REPEATER DEFECTS ON A SEMICONDUCTOR WAFER

(71) Applicant: KLA-TENCOR CORPORATION, Milpitas, CA (US)

(72) Inventors: Bjorn Brauer, Beaverton, OR (US); Hucheng Lee, Cupertino, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 16/101,553

(22) Filed: Aug. 13, 2018

(65) Prior Publication Data

US 2019/0346376 A1    Nov. 14, 2019

Related U.S. Application Data

(60) Provisional application No. 62/669,361, filed on May 9, 2018.

(51) Int. Cl.
  *G01N 21/95* (2006.01)
  *G01N 21/88* (2006.01)

(52) U.S. Cl.
  CPC ..... *G01N 21/9501* (2013.01); *G01N 21/8806* (2013.01); *G01N 21/8851* (2013.01)

(58) Field of Classification Search
  CPC .......... G01N 21/9501; G01N 21/8806; G01N 21/8851
  USPC ...................... 356/237.1–237.6, 239.1–239.8
  See application file for complete search history.

(56) References Cited

U.S. PATENT DOCUMENTS

| | | |
|---|---|---|
| 2009/0041332 A1 | 2/2009 | Bhaskar et al. |
| 2009/0274981 A1 | 11/2009 | Griebenow et al. |
| 2010/0076699 A1 | 3/2010 | Auerbach |
| 2015/0012900 A1 | 1/2015 | Shifrin et al. |
| 2016/0061745 A1 | 3/2016 | Chen et al. |
| 2016/0061749 A1 | 3/2016 | Chen et al. |

FOREIGN PATENT DOCUMENTS

| | | |
|---|---|---|
| JP | 11087443 A | 3/1999 |
| JP | 2004117229 A | 4/2004 |
| KR | 20080026574 A | 3/2008 |

OTHER PUBLICATIONS

WIPO, ISR for PCT/US2019/030516, Aug. 12, 2019.
WIPO, ISR for PCT/US2019/031399, Aug. 22, 2019.

*Primary Examiner* — Tri T Ton
(74) *Attorney, Agent, or Firm* — Hodgson Russ LLP

(57) ABSTRACT

Repeater analysis at a first threshold identifies repeater defects. The repeater defects are located at a coordinate that is the same on each reticle. Images on every reticle of the semiconductor wafer at the coordinate are received, and a plurality of signed difference images are obtained. A repeater threshold for signed difference images is calculated, as is consistency of the polarity. The threshold is applied to the images and a number of defects per each repeater that remain are determined. A secondary repeater threshold can be applied for nuisance filtering.

20 Claims, 5 Drawing Sheets

Wafer map

Reticle stack

FIG. 4

CAPTURE OF REPEATER DEFECTS ON A SEMICONDUCTOR WAFER

CROSS-REFERENCE TO RELATED APPLICATIONS

This application claims priority to the provisional patent application filed May 9, 2018 and assigned U.S. App. No. 62/669,361, the disclosure of which is hereby incorporated by reference.

FIELD OF THE DISCLOSURE

This disclosure relates to defect detection.

BACKGROUND OF THE DISCLOSURE

Evolution of the semiconductor manufacturing industry is placing ever greater demands on yield management and, in particular, on metrology and inspection systems. Critical dimensions continue to shrink, yet the industry needs to decrease the time for achieving high-yield, high-value production. Minimizing the total time from detecting a yield problem to fixing it determines the return-on-investment for a semiconductor manufacturer.

Fabricating semiconductor devices, such as logic and memory devices, typically includes processing a semiconductor wafer using a large number of fabrication processes to form various features and multiple levels of the semiconductor devices. For example, lithography is a semiconductor fabrication process that involves transferring a pattern from a reticle to a photoresist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Defect review for advanced design rules can search for objects that are quite small (e.g., for detection of defects in 10 nm range), so hot scans may be run to catch such defects. A "hot scan" generally refers to a measurement/inspection of a wafer performed to detect defects or take measurements on the wafer by applying relatively aggressive detection settings (e.g., thresholds substantially close to the noise floor). In this manner, the hot scan may be performed to collect inspection or measurement data about the wafer that will be used for the tuning process (e.g., optics selection and algorithm tuning). The goal of the hot scan may be to detect a representative sample of all defect and nuisance types on the wafer in the selected mode(s).

Repeater defects are a concern to semiconductor manufacturers. Repeater defects are those defects that appear on a wafer with some regular periodicity and that show some fixed relationship to the die layout on a reticle or stepping pattern on a wafer. Reticle defects are a common cause of repeater defects. Reticle defects that can cause repeater defects include, for example, extra chrome pattern on a mask plate, missing chrome on a mask plate, particulates on the mask plate or on the reticle, and damage to the pellicle.

Repeater filtering (e.g., with coordinates matching) can be a strong filter that can bring the nuisance density to manageable levels. However, hot inspections required for mask qualification may result in billions of defect candidates. It should be noted that repeater defects can be "soft" repeaters. Soft repeaters are not printed in every reticle due to process variation. This means that it may not be possible to use in-job repeater defect detection (RDD) while being able to analyze results for the whole wafer.

With feature shrink and a potential resolution limit for optical wafer inspection tools, the primary candidate inspection tool for print check is an electron beam inspection tool, such as a scanning electron microscope (SEM). However, electron beam inspection tools have a throughput disadvantage. With the best scenario of multiple beam/column options, the estimated inspection time for one reticle is more than eight hours. Broadband plasma (BBP) tools have much higher throughput and, hence, coverage. In the current BBP tool design, repeater analysis is part of the post-processing step in the high level defect detection controller and a current implementation of RDD supports up to 10 billion defects for initial defect detection.

Current defect detection algorithms perform defect detection in a chronologic way meaning the algorithms inspect swath after swath without ever coming back to the previous swath to apply the learning of the new swath to the old one. Current methods, such as multi-die adaptive threshold (MDAT), standard reference die (SRD), or NanoMDAT, have similar disadvantages. First, the nuisance rate is high and the repeater capture rate is low. Second, these techniques do not use information that the defects are repeater defects to improve detectability. Third, many parameters need to be used for time-consuming nuisance tuning.

These three previous techniques also have disadvantages compared to individual algorithms. MDAT and NanoMDAT both require double detection for single die-to-die comparisons for every additional defect that needs to be detected. SRD and MDAT both calculate noise from the entire image frame, which is usually 1 k×1 k pixels$^2$. The noise can have a low signal-to-noise ratio because there can be many noise sources within an image frame.

Therefore, new repeater defect detection techniques and systems are needed.

BRIEF SUMMARY OF THE DISCLOSURE

A method is provided in a first embodiment. The method includes performing, using the processor, repeater analysis on a semiconductor wafer at a first threshold to remove non-repeater defects and identify repeater defects. The repeater defects are located at a coordinate that is the same on each reticle. Images on every reticle of the semiconductor wafer at the coordinate are received at the processor. A plurality of signed difference images are obtained using the processor. Each of the signed difference images is for one of the images at the coordinate. A mean normalized value is calculated for the signed difference images using the processor. A consistency of a polarity in the signed difference images is evaluated using the processor. A repeater threshold is applied to the images using the processor. A number of defects that remain at the coordinate after the repeater threshold is applied is determined using the processor. The repeater threshold is set using the processor thereby providing a filter for nuisance.

The method can further include performing a hot scan of the semiconductor wafer. Results from the hot scan are used for the repeater analysis.

Obtaining the difference image can include a single detection algorithm. Obtaining the difference image also can include a double detection algorithm. With a double detection algorithm, the signed difference image is used with a higher absolute repeater threshold per coordinate.

The mean normalized value can be calculated using an equation $$\frac{(\text{defect value} - \text{mean})}{\text{standard deviation}}.$$

If repeater threshold is a maximum, then the defect is a bright polarity defect. If the repeater threshold is a minimum, then the defect is a dark polarity defect.

The method can further include sending instructions, using the processor, to image all of the reticles at a location of the repeater defect.

The method can further include filtering, using the processor, the images using the repeater threshold that is set.

Calculating the repeater threshold can includes evaluating a number of defects with bright polarity and a number of defects with dark polarity. A larger of the number of defects with bright polarity and the number of defects with dark polarity may be used with the repeater threshold.

A non-transitory computer readable medium storing a program configured to instruct the processor to execute one of the instances of the first embodiment can be provided.

A system is provided in a second embodiment. The system comprises a broadband plasma tool and a processor in electronic communication with the broadband plasma tool. The broadband plasma tool includes a stage configured to hold a semiconductor wafer, a light source configured to direct light at the semiconductor wafer, and a detector configured to receive light reflected from the semiconductor wafer and generate an image. The processor is configured to perform repeater analysis on a semiconductor wafer at a first threshold to remove non-repeater defects and identify repeater defects; receive images on every reticle of the semiconductor wafer at the coordinate; obtain a plurality of signed difference images; calculate a mean normalized value for the signed difference images; evaluate a consistency of a polarity in the signed difference images; apply the repeater threshold to the images; determine a number of defects that remain at the coordinate after the threshold is applied; and set a repeater threshold thereby providing a filter for nuisance. The repeater defects are located at a coordinate that is the same on each reticle. Each of the signed difference images is for one of the images at the coordinate.

The light source may be one of a deep ultraviolet, ultraviolet, or variable illumination spectrum source.

Obtaining the difference image can include a single detection algorithm. Obtaining the difference image also can include a double detection algorithm. The signed difference image is used with a higher absolute repeater threshold per coordinate with the double detection algorithm.

The mean normalized value can be calculated using an equation $$\frac{(\text{defect value} - \text{mean})}{\text{standard deviation}}.$$

The repeater threshold may be a maximum, and the defect may be a bright polarity defect.

The mean normalized value can be calculated using an equation $$\frac{(\text{defect value} - \text{mean})}{\text{standard deviation}}.$$

The repeater threshold may be a minimum, and the defect may be a dark polarity defect.

The processor can be configured to send instructions to image all of the reticles at a location of the repeater defect.

The processor can be configured to filter the images using the repeater threshold that is set.

DESCRIPTION OF THE DRAWINGS

For a fuller understanding of the nature and objects of the disclosure, reference should be made to the following detailed description taken in conjunction with the accompanying drawings, in which:

FIG. 4 shows an exemplary set of eighteen reticles; and

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

Embodiments of repeater defect detection disclosed herein can include a dual algorithm approach. First, a hot scan is performed and the results are analyzed with, for example, an MDAT or SRD algorithm. Then image data can be collected at all the potential repeater locations to perform statistical analysis. The single detection can use a maximum difference of the two reference minus candidate image pairs. Polarity consistency analysis can be performed. Thus, only repeater defects that are captured in larger numbers (i.e., bright or dark) are kept.

Figure 1:
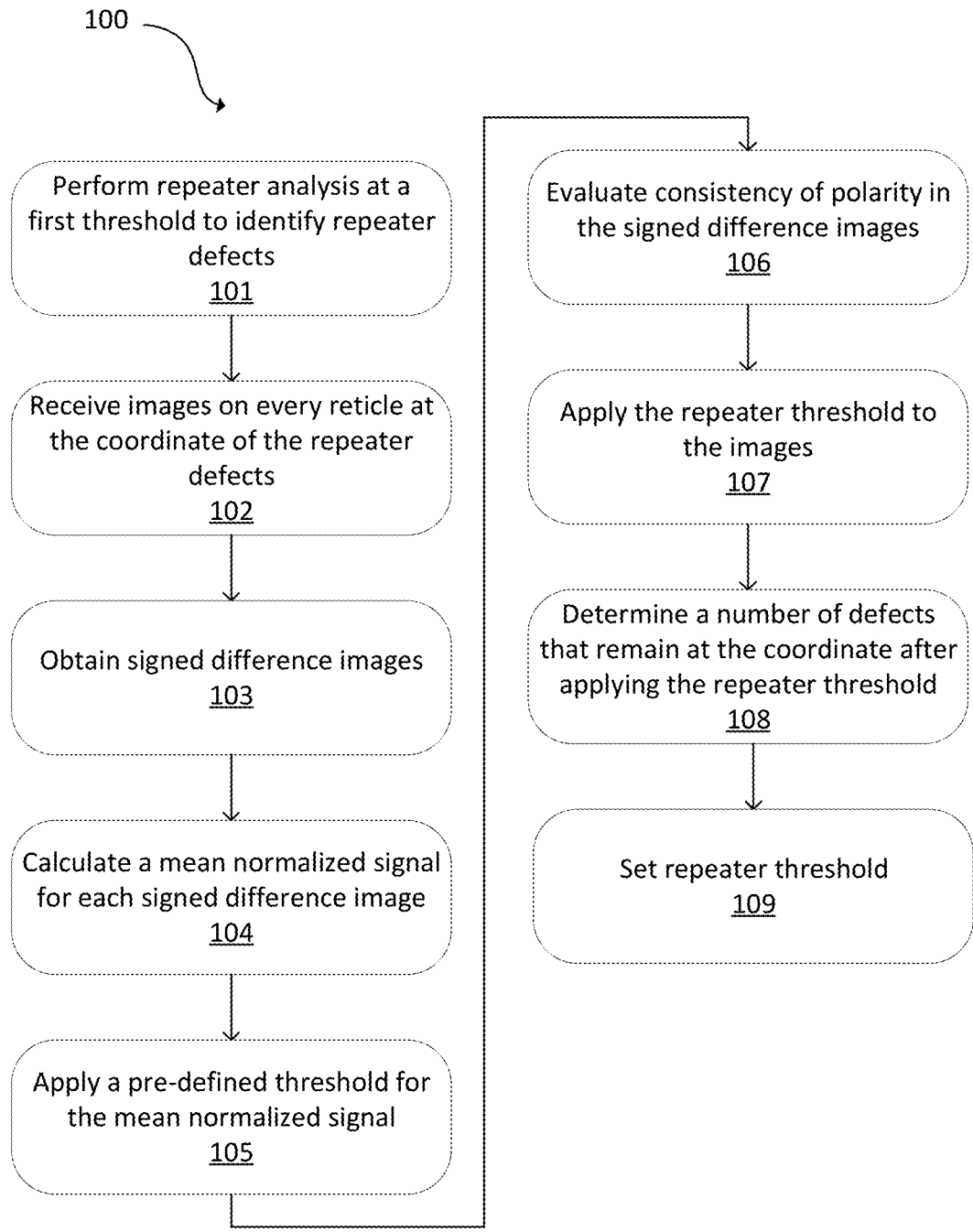
FIG. 1 is a flowchart illustrating an embodiment of a method in accordance with the present disclosure.

FIG. 1 is a flowchart of a method 100. One or more steps of the method 100 can use a processor.

At 101, repeater analysis is performed on a semiconductor wafer at a first threshold. The first threshold removes non-repeater defects and identifies repeater defects. The repeater defects are located at a coordinate that is the same on each reticle. Soft repeaters can be identified.

A hot scan of the semiconductor wafer can be performed. Results from the hot scan can be used for the repeater analysis. For example, MDAT or SRD can be used to analyzed data from the hot scan. The number of unique repeaters after the repeater analysis can be denoted as n.

In an instance, the repeater defect locations may be found with robust average algorithms such as repeater in array (RIA) or standard reference die (SRD) for logic areas or die-to-die inspections. Robust average algorithms calculate the average of a certain number of reference frames and remove outliers such as single pixel noise. The robust average algorithms may allow the scan to run hotter than die-to-die inspections, but die-to-die inspections can still be used. RIA averages many cells within an array and compares them to the candidate image. SRD calculates a reference image on a golden (e.g., a reference or clean) die on a reference wafer. This then can be compared to an image on the inspection wafer, and the difference image will be calculated.

At 102, images on every reticle of the semiconductor wafer at the reticle coordinate of the repeater defects are received. Instructions may be sent to image all the reticles at a location of the repeater defect. This may be performed by a wafer inspection tool, such as an SEM, or by the BBP tool.

For example, the repeater defects from 101 can be used to collect 32×32 pixel$^2$ image data at the same reticle location for all recorded reticles (the count denoted as r) for all defects. This assumes that reticles are aligned. This results in n×r×3 images for MDAT. The factor of three exists because there is a defective image and two reference images for each site. This results in n×r×2 images for SRD. The factor of two exists because there is a defective image and one reference image for each site. The number of unique repeaters after the repeater analysis can be denoted as n and defects with the same repeater identity can be denoted as r.

A plurality of signed difference images are obtained at 103. One or more signed difference images are obtained at each site. Each of the signed difference images may be for one of the images at the coordinate of the repeater defects. Obtaining the signed difference images can include a single detection algorithm or a double detection algorithm. Note that there is only one reference image for SRD, so there is only one signed difference image.

The terminology "signed" is used to differentiate from often-used procedures to calculate the difference image in which the grey levels of the candidate image are subtracted from the grey levels of the reference image and the absolute for each pixel is reported. The sign of the difference, which contains valuable information, is lost. Namely, this can lose whether the defect in the candidate image is brighter or darker than the defect in the reference image. For repeater defects it is expected that all the sites for the same repeater defect have the exact same sign. This can be referred to as polarity. If the sign varies for a given repeater for different reticles then this is an indication that it may be a nuisance. This consistency can be used in polarity to filter out nuisance events.

Double detection may be used because whether the defect is in the candidate or the reference will not be known if candidates are compared versus one reference. If a second reference is used and the same difference signal between candidate and reference exists, then the defect must be in the candidate.

Single detection is used when it is known that the reference has no defect. For example, in SRD a clean reference is used. "Clean" means that whether there are any additional defects compared to this clean (i.e., golden) reference is the only information that is determined. Single detection is also used if the reference was calculated from the median of several reference images because in this case the median image calculation will not have defects in it because the median is removing these outliers.

A mean normalized value for the signed difference images is calculated at 104. In an instance, the normalization can be performed by dividing the difference of the signal (i.e., the defect value) minus the mean by the standard deviation. In this instance, the mean and standard deviation are of the signed difference images. The mean normalized value may be a maximum if the defect is a bright polarity defect. The mean normalized value may be a minimum if the defect is a dark polarity defect. With respect to dark and bright defects, the equation that results in the larger absolute value per site may be used for further analysis.

The mean normalized value may be calculated using the following equation.

$$\frac{(\text{defect value} - \text{mean})}{\text{standard deviation}}$$

In this equation, the mean normalized value may be a maximum if the defect is a bright polarity defect. The mean normalized value also may be a minimum if the defect is a dark polarity defect.

Other calculations besides the mean normalized value equation can be performed to determine if a signal is present. For example, raw signal (e.g., difference grey level) or other defect attributes that can be calculated based on a patch image can be used. Defect shape or defect size can be calculated. In another example, a neural network is trained on defects of interest (DOI) and nuisance examples. This neural network can use a derived attribute, such as a logit value, to determine if a defect is present in a given collected patch image or not.

At 105, for defects with the same repeater identity (r repeaters each), the number of defects with dark polarity and bright polarity can be evaluated after applying a pre-defined threshold to the mean normalized value has been applied. Either dark polarity or bright polarity defects can be used depending on which count is larger. The pre-defined threshold can be set by a user.

Consistency of the polarity in the signed difference images is evaluated at 106. If there are more bright polarity defects per repeater then the count of the bright polarity defects will be used for further analysis. If there are more dark polarity defects per repeater then the count of the dark polarity defects will be used for further analysis A repeater threshold is applied to the images at 107. In an embodiment, all repeaters can be sorted based on the number of captured defects per repeater. Then, for example, the 1000 repeaters with the highest capture rate are selected for SEM review.

At 108, a number of defects that remain at the coordinate after the repeater threshold is applied is determined. The number of defects can be per each repeater defect. For example, the repeater threshold can be set and the number of remaining defects per repeater identification can be reported. Repeaters with the highest repeater count per repeater identification can be reviewed using an SEM to determine if those repeaters are defects of interest or nuisance.

For example, 5000 repeaters are captured in less than 50% of the reticles, 600 repeaters are captured in 50-60% of the reticles, and 400 repeaters are captured more than 60% of the reticles. Depending on the SEM review budget, the user could set a threshold at 60% capture. The user also could have an SEM review budget of 1000 repeaters, and the user could review the top 1000 repeaters, which in this case are all those that are captured more often than 50% of the time.

The repeater threshold can be set by a user at 109, and may be based on the results from step 108. The repeater threshold can change between sets of images or even after the repeater threshold is applied to the images. This can provide a filter for nuisance. The nuisance events will have a lower repeater capture rate than the defects of interest. Tuning the repeater threshold can reduce the nuisance rate. This may be because, for example, nuisance events are unlikely to occur at the same position across multiple reticles.

The repeater threshold may be unique to an individual wafer or may be applied to other wafers with similar designs.

Embodiments of method 100 only require a single detection, which increases sensitivity. A local (e.g., patch image-based) signal can be used for the analysis. Only defects with the same polarity may be considered. In an instance, either the majority of the defective images are brighter or darker than the reference image.

Embodiments of the method 100 are compatible with SRD and can help improve single die reticle repeater defect capture rate.

Embodiments of the method 100 can enable higher repeater capture rate and lower nuisance rate because not every repeater location needs to pass the first detection threshold if it has enough local consistent salient signal. Furthermore, nuisance tuning is less time-consuming because there is typically only the repeater threshold that needs to be adjusted.

Figure 2:
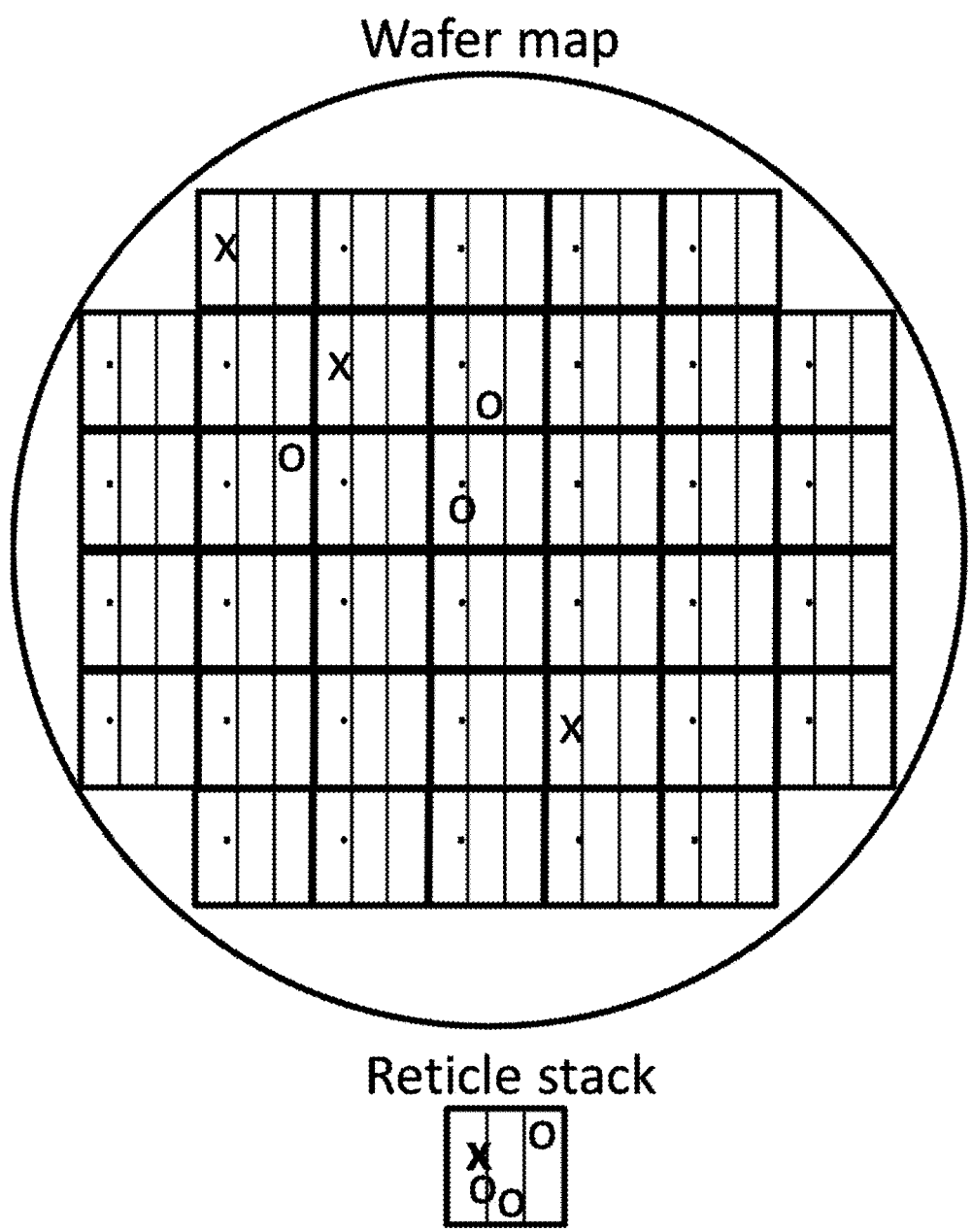
FIG. 2 is a wafer map and reticle stack of a reticle including three dies per reticle.

FIG. 2 is a wafer map and reticle stack of a reticle including three dies per reticle. All defects marked as X are located at the same reticle coordinate and are repeaters. All defects marked O occur at different reticle locations and are not repeaters. In the example of FIG. 2, a detection algorithm like MDAT detects defects in a hot scan. If those defects have the same reticle coordinate then the defects are considered as repeater defects. Image data is collected at the same location for all the reticles (e.g., imaging the coordinate with the repeater defect). This is marked with a dot.

Figure 3:
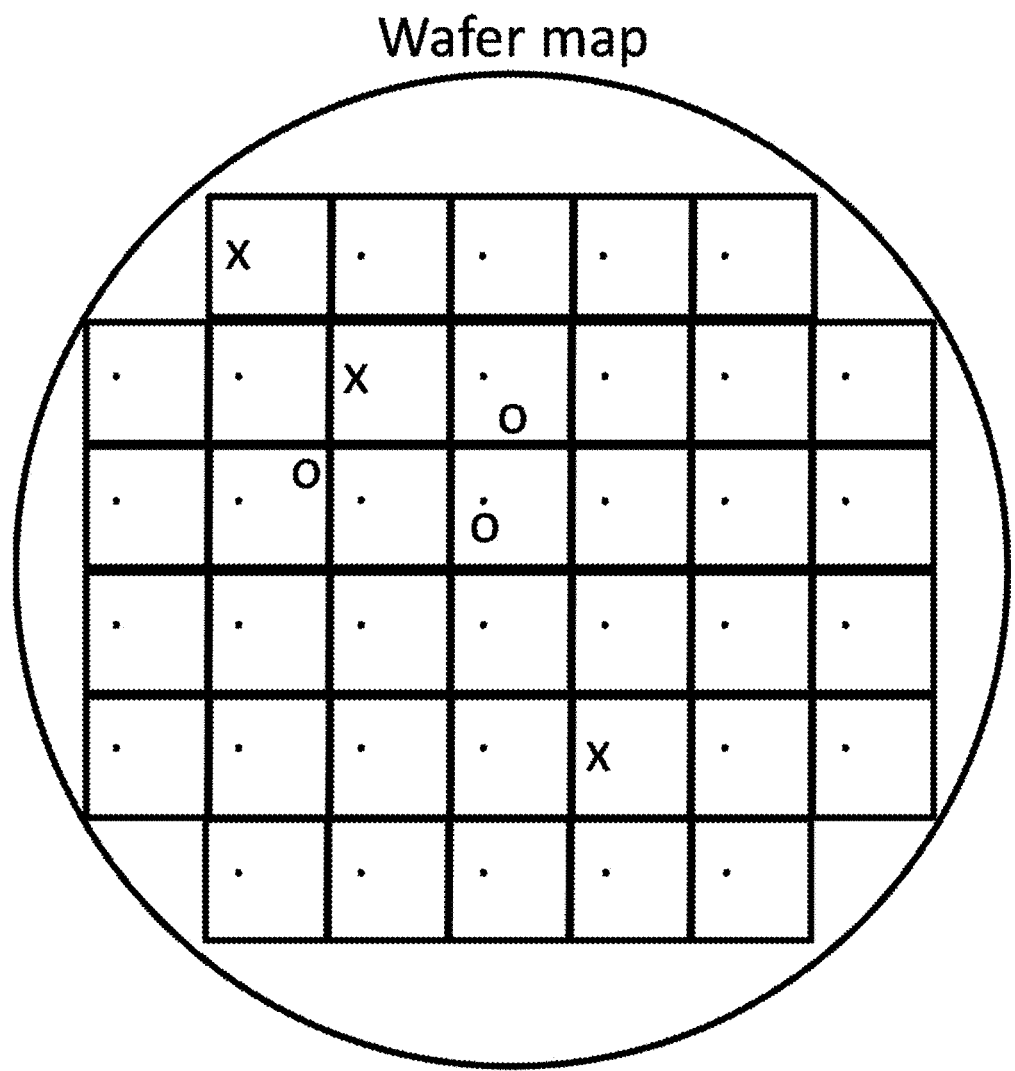
FIG. 3 is a wafer map and reticle stack of a reticle including one die per reticle.
Figure 3:
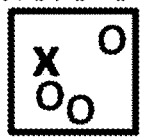

FIG. 3 is a wafer map and reticle stack of a reticle including one die per reticle. All defects marked as X are located at the same reticle coordinate and are repeaters. All defects marked O occur at different reticle locations and are not repeaters. In the example of FIG. 3, a detection algorithm like SRD detects defects in a hot scan. If those defects have the same reticle coordinate then the defects are considered as repeater defects. Image data is collected at the same location for all the reticles (e.g., imaging the coordinate with the repeater defect). This is marked with a dot.

The method 100 is not limited to the number of dies per reticle illustrated herein. The method 100 can be used with any integer number of dies per reticle used in the semiconductor industry. Thus, the method 100 can be used with one, two, four, sixteen, or other numbers of dies per reticle.

Figure 4:
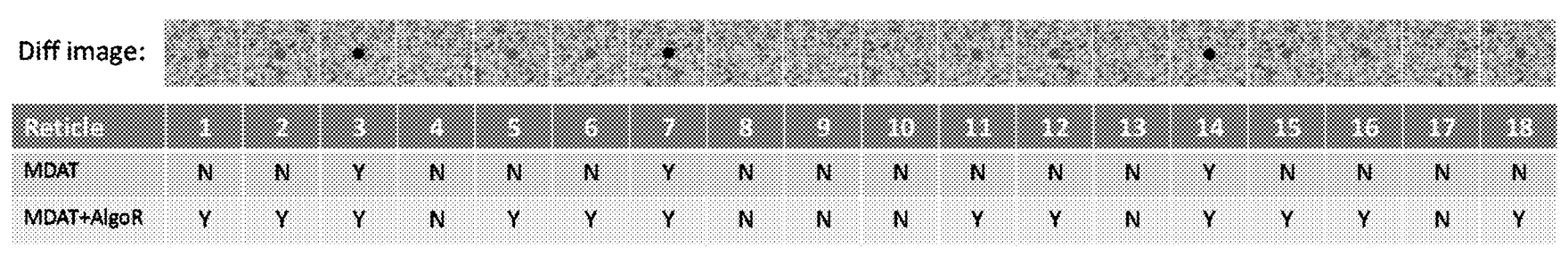

FIG. 4 is an example showing eighteen reticles. The table shows a difference image ("Diff image") for each reticle with the defect in the center at the same reticle location for those eighteen reticles on the wafer. The defect is a black (strong signal) or grey (weak signal) circle in the center of the images. The images are collected after, for example, MDAT detected some repeater defects in at least two of the eighteen reticles.

By itself, MDAT only caught three of the eighteen repeater defects. MDAT with the repeater threshold of method 100 (designated as "MDAT+AlgoR") detects the same three defects when running the initial MDAT hot scan, then learns that these are repeater defects and collects image data for the same reticle coordinate in all the eighteen reticles. In this example, twelve of the defects are captured using MDAT+AlgoR with the repeater threshold of method 100. This is shown with the yes ("Y") and no ("N") entries indicating whether the defect was captured using the particular methods. If all the defects of interest are showing such a behavior, a repeater threshold of twelve can be used to filter out nuisance. This will result in a reduction of nuisance rate.

Figure 5:
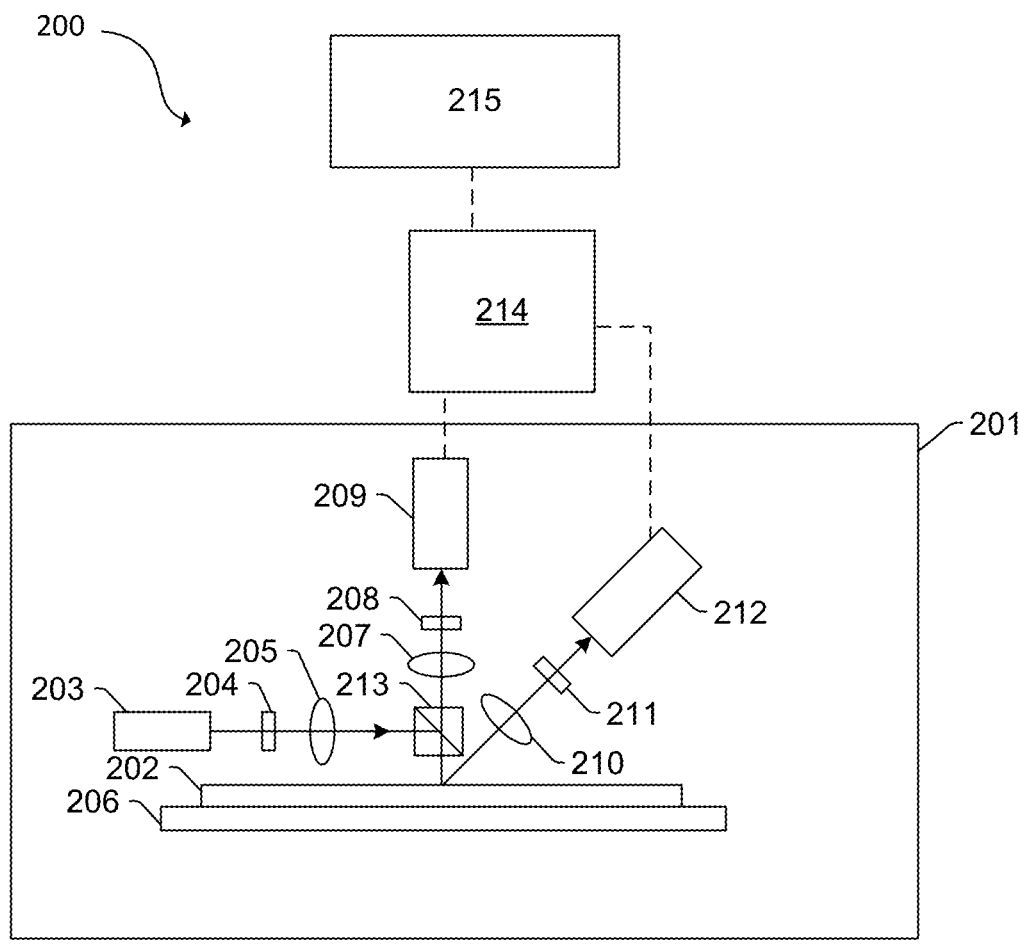
FIG. 5 is a diagram of a system embodiment in accordance with the present disclosure.

One embodiment of a system 200 is shown in FIG. 5. The system 200 includes optical based subsystem 201. In general, the optical based subsystem 201 is configured for generating optical based output for a specimen 202 by directing light to (or scanning light over) and detecting light from the specimen 202. In one embodiment, the specimen 202 includes a wafer. The wafer may include any wafer known in the art. In another embodiment, the specimen includes a reticle. The reticle may include any reticle known in the art.

In the embodiment of the system 200 shown in FIG. 5, optical based subsystem 201 includes an illumination subsystem configured to direct light to specimen 202. The illumination subsystem includes at least one light source. For example, as shown in FIG. 5, the illumination subsystem includes light source 203. In one embodiment, the illumination subsystem is configured to direct the light to the specimen 202 at one or more angles of incidence, which may include one or more oblique angles and/or one or more normal angles. For example, as shown in FIG. 5, light from light source 203 is directed through optical element 204 and then lens 205 to specimen 202 at an oblique angle of incidence. The oblique angle of incidence may include any suitable oblique angle of incidence, which may vary depending on, for instance, characteristics of the specimen 202.

The optical based subsystem 201 may be configured to direct the light to the specimen 202 at different angles of incidence at different times. For example, the optical based subsystem 201 may be configured to alter one or more characteristics of one or more elements of the illumination subsystem such that the light can be directed to the specimen 202 at an angle of incidence that is different than that shown in FIG. 5. In one such example, the optical based subsystem 201 may be configured to move light source 203, optical element 204, and lens 205 such that the light is directed to the specimen 202 at a different oblique angle of incidence or a normal (or near normal) angle of incidence.

In some instances, the optical based subsystem 201 may be configured to direct light to the specimen 202 at more than one angle of incidence at the same time. For example, the illumination subsystem may include more than one illumination channel, one of the illumination channels may include light source 203, optical element 204, and lens 205 as shown in FIG. 5 and another of the illumination channels (not shown) may include similar elements, which may be configured differently or the same, or may include at least a light source and possibly one or more other components such as those described further herein. If such light is directed to the specimen at the same time as the other light, one or more characteristics (e.g., wavelength, polarization, etc.) of the light directed to the specimen 202 at different angles of incidence may be different such that light resulting from illumination of the specimen 202 at the different angles of incidence can be discriminated from each other at the detector(s).

In another instance, the illumination subsystem may include only one light source (e.g., light source 203 shown in FIG. 5) and light from the light source may be separated into different optical paths (e.g., based on wavelength, polarization, etc.) by one or more optical elements (not shown) of the illumination subsystem. Light in each of the different optical paths may then be directed to the specimen 202. Multiple illumination channels may be configured to direct light to the specimen 202 at the same time or at different times (e.g., when different illumination channels are used to sequentially illuminate the specimen). In another instance, the same illumination channel may be configured to direct light to the specimen 202 with different characteristics at different times. For example, in some instances, optical element 204 may be configured as a spectral filter and the properties of the spectral filter can be changed in a variety of different ways (e.g., by swapping out the spectral filter) such that different wavelengths of light can be directed to the specimen 202 at different times. The illumination subsystem may have any other suitable configuration known in the art for directing the light having different or the same characteristics to the specimen 202 at different or the same angles of incidence sequentially or simultaneously.

In one embodiment, light source 203 may include a broadband plasma (BBP) source. In this manner, the light generated by the light source 203 and directed to the specimen 202 may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source 203 may also include a polychromatic light source that generates light at multiple discrete wavelengths or wavebands.

Light from optical element 204 may be focused onto specimen 202 by lens 205. Although lens 205 is shown in FIG. 5 as a single refractive optical element, it is to be understood that, in practice, lens 205 may include a number of refractive and/or reflective optical elements that in combination focus the light from the optical element to the specimen. The illumination subsystem shown in FIG. 5 and described herein may include any other suitable optical elements (not shown). Examples of such optical elements include, but are not limited to, polarizing component(s), spectral filter(s), spatial filter(s), reflective optical element(s), apodizer(s), beam splitter(s) (such as beam splitter 213), aperture(s), and the like, which may include any such suitable optical elements known in the art. In addition, the optical based subsystem 201 may be configured to alter one or more of the elements of the illumination subsystem based on the type of illumination to be used for generating the optical based output.

The optical based subsystem 201 may also include a scanning subsystem configured to cause the light to be scanned over the specimen 202. For example, the optical based subsystem 201 may include stage 206 on which specimen 202 is disposed during optical based output generation. The scanning subsystem may include any suitable mechanical and/or robotic assembly (that includes stage 206) that can be configured to move the specimen 202 such that the light can be scanned over the specimen 202. In addition, or alternatively, the optical based subsystem 201 may be configured such that one or more optical elements of the optical based subsystem 201 perform some scanning of the light over the specimen 202. The light may be scanned over the specimen 202 in any suitable fashion such as in a serpentine-like path or in a spiral path.

The optical based subsystem 201 further includes one or more detection channels. At least one of the one or more detection channels includes a detector configured to detect light from the specimen 202 due to illumination of the specimen 202 by the subsystem and to generate output responsive to the detected light. For example, the optical based subsystem 201 shown in FIG. 5 includes two detection channels, one formed by collector 207, element 208, and detector 209 and another formed by collector 210, element 211, and detector 212. As shown in FIG. 5, the two detection channels are configured to collect and detect light at different angles of collection. In some instances, both detection channels are configured to detect scattered light, and the detection channels are configured to detect tight that is scattered at different angles from the specimen 202. However, one or more of the detection channels may be configured to detect another type of light from the specimen 202 (e.g., reflected light).

As further shown in FIG. 5, both detection channels are shown positioned in the plane of the paper and the illumination subsystem is also shown positioned in the plane of the paper. Therefore, in this embodiment, both detection channels are positioned in (e.g., centered in) the plane of incidence. However, one or more of the detection channels may be positioned out of the plane of incidence. For example, the detection channel formed by collector 210, element 211, and detector 212 may be configured to collect and detect light that is scattered out of the plane of incidence. Therefore, such a detection channel may be commonly referred to as a "side" channel, and such a side channel may be centered in a plane that is substantially perpendicular to the plane of incidence.

Although FIG. 5 shows an embodiment of the optical based subsystem 201 that includes two detection channels, the optical based subsystem 201 may include a different number of detection channels (e.g., only one detection channel or two or more detection channels). In one such instance, the detection channel formed by collector 210, element 211, and detector 212 may form one side channel as described above, and the optical based subsystem 201 may include an additional detection channel (not shown) formed as another side channel that is positioned on the opposite side of the plane of incidence. Therefore, the optical based subsystem 201 may include the detection channel that includes collector 207, element 208, and detector 209 and that is centered in the plane of incidence and configured to collect and detect light at scattering angle(s) that are at or close to normal to the specimen 202 surface. This detection channel may therefore be commonly referred to as a "top" channel, and the optical based subsystem 201 may also include two or more side channels configured as described above. As such, the optical based subsystem 201 may include at least three channels (i.e., one top channel and two side channels), and each of the at least three channels has its own collector, each of which is configured to collect light at different scattering angles than each of the other collectors.

As described further above, each of the detection channels included in the optical based subsystem 201 may be configured to detect scattered light. Therefore, the optical based subsystem 201 shown in FIG. 5 may be configured for dark field (DF) output generation for specimens 202. However, the optical based subsystem 201 may also or alternatively include detection channel(s) that are configured for bright field (BF) output generation for specimens 202. In other words, the optical based subsystem 201 may include at least one detection channel that is configured to detect light specularly reflected from the specimen 202. Therefore, the optical based subsystems 201 described herein may be configured for only DF, only BF, or both DF and BF imaging. Although each of the collectors are shown in FIG. 5 as single refractive optical elements, it is to be understood that each of the collectors may include one or more refractive optical die(s) and/or one or more reflective optical element(s).

The one or more detection channels may include any suitable detectors known in the art. For example, the detectors may include photo-multiplier tubes (PMTs), charge coupled devices (CCDs), time delay integration (TDI) cameras, and any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the optical based subsystem may be signals or data, but not image signals or image data. In such instances, a processor such as processor 214 may be configured to generate images of the specimen 202 from the non-imaging output of the detectors. However, in other instances, the detectors may be configured as imaging detectors that are configured to generate imaging signals or image data. Therefore, the optical based subsystem may be configured to generate optical images or other optical based output described herein in a number of ways.

It is noted that FIG. 5 is provided herein to generally illustrate a configuration of an optical based subsystem 201 that may be included in the system embodiments described herein or that may generate optical based output that is used by the system embodiments described herein. The optical based subsystem 201 configuration described herein may be altered to optimize the performance of the optical based subsystem 201 as is normally performed when designing a commercial output acquisition system. In addition, the systems described herein may be implemented using an existing system (e.g., by adding functionality described herein to an existing system). For some such systems, the methods described herein may be provided as optional functionality of the system (e.g., in addition to other functionality of the system). Alternatively, the system described herein may be designed as a completely new system.

The processor 214 may be coupled to the components of the system 200 in any suitable manner (e.g., via one or more transmission media, which may include wired and/or wireless transmission media) such that the processor 214 can receive output. The processor 214 may be configured to perform a number of functions using the output. The system 200 can receive instructions or other information from the processor 214. The processor 214 and/or the electronic data storage unit 215 optionally may be in electronic communication with a wafer inspection tool, a wafer metrology tool, or a wafer review tool (not illustrated) to receive additional information or send instructions. For example, the processor 214 and/or the electronic data storage unit 215 can be in electronic communication with an SEM.

The processor 214, other system(s), or other subsystem(s) described herein may be part of various systems, including a personal computer system, image computer, mainframe computer system, workstation, network appliance, internet appliance, or other device. The subsystem(s) or system(s) may also include any suitable processor known in the art, such as a parallel processor. In addition, the subsystem(s) or system(s) may include a platform with high-speed processing and software, either as a standalone or a networked tool.

The processor 214 and electronic data storage unit 215 may be disposed in or otherwise part of the system 200 or another device. In an example, the processor 214 and electronic data storage unit 215 may be part of a standalone control unit or in a centralized quality control unit. Multiple processors 214 or electronic data storage units 215 may be used.

The processor 214 may be implemented in practice by any combination of hardware, software, and firmware. Also, its functions as described herein may be performed by one unit, or divided up among different components, each of which may be implemented in turn by any combination of hardware, software and firmware. Program code or instructions for the processor 214 to implement various methods and functions may be stored in readable storage media, such as a memory in the electronic data storage unit 215 or other memory.

If the system 200 includes more than one processor 214, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media known in the art. Two or more of such subsystems may also be effectively coupled by a shared computer-readable storage medium (not shown).

The processor 214 may be configured to perform a number of functions using the output of the system 200 or other output. For instance, the processor 214 may be configured to send the output to an electronic data storage unit 215 or another storage medium. The processor 214 may be further configured as described herein.

If the system includes more than one subsystem, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media known in the art. Two or more of such subsystems may also be effectively coupled by a shared computer-readable storage medium (not shown).

The processor 214 may be configured according to any of the embodiments described herein. The processor 214 also may be configured to perform other functions or additional steps using the output of the system 200 or using images or data from other sources.

Various steps, functions, and/or operations of system 200 and the methods disclosed herein are carried out by one or more of the following: electronic circuits, logic gates, multiplexers, programmable logic devices, ASICs, analog or digital controls/switches, microcontrollers, or computing systems. Program instructions implementing methods such as those described herein may be transmitted over or stored on carrier medium. The carrier medium may include a storage medium such as a read-only memory, a random access memory, a magnetic or optical disk, a non-volatile memory, a solid state memory, a magnetic tape, and the like. A carrier medium may include a transmission medium such as a wire, cable, or wireless transmission link. For instance, the various steps described throughout the present disclosure may be carried out by a single processor 214 or, alternatively, multiple processors 214. Moreover, different subsystems of the system 200 may include one or more computing or logic systems. Therefore, the above description should not be interpreted as a limitation on the present disclosure but merely an illustration.

In an instance, the processor 214 is in communication with the system 200, which may use a BBP. The light source is one of a deep ultraviolet, ultraviolet, or variable illumination spectrum source. The processor 214 is configured to perform repeater analysis on a semiconductor wafer at a first threshold to remove non-repeater defects and identify repeater defects. The repeater defects are located at a coordinate that is the same on each reticle. The processor 214 is also configured to receive images on every reticle of the semiconductor wafer at the coordinate. The processor 214 is also configured to obtain a plurality of signed difference images. Each of the signed difference images is for one of the images at the coordinate. The processor 214 is also configured to calculate a mean normalized value for the signed difference images, evaluate a consistency of a polarity in the signed difference images, apply the repeater threshold to the images, determine a number of defects that remain at the coordinate after the threshold is applied, and set a repeater threshold thereby providing a filter for nuisance.

Obtaining the difference image can include a single detection algorithm or a double detection algorithm. For a double detection algorithm, the signed difference image is used with the higher absolute mean normalized value.

The mean normalized value may be calculated using the equation $$\frac{(\text{defect value} - \text{mean})}{\text{standard deviation}}.$$

The mean normalized value may be a maximum if the defect is a bright polarity defect. The mean normalized value also may be a minimum if the defect is a dark polarity defect.

The processor 214 can be configured to send instructions to image all of the reticles at a location of the repeater defect.

The images using the repeater threshold that is set can be filtered, such as using the processor 214.

An additional embodiment relates to a non-transitory computer-readable medium storing program instructions executable on a controller for performing a computer-implemented method for determining a height of an illuminated region on a surface of a specimen 202, as disclosed herein. In particular, as shown in FIG. 5, electronic data storage unit 215 or other storage medium may contain non-transitory computer-readable medium that includes program instructions executable on the processor 214. The computer-implemented method may include any step(s) of any method(s) described herein, including method 100.

Program instructions implementing methods such as those described herein may be stored on computer-readable medium, such as in the electronic data storage unit 215 or other storage medium. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes (MFC), Streaming SIMD Extension (SSE), or other technologies or methodologies, as desired.

Each of the steps of the method may be performed as described herein. The methods also may include any other step(s) that can be performed by the processor and/or computer subsystem(s) or system(s) described herein. The steps can be performed by one or more computer systems, which may be configured according to any of the embodiments described herein. In addition, the methods described above may be performed by any of the system embodiments described herein.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. A method comprising:
   performing, using the processor, repeater analysis on a semiconductor wafer at a first threshold to remove non-repeater defects and identify repeater defects, wherein the repeater defects are located at a coordinate that is the same on each reticle;
   receiving, at the processor, images on every reticle of the semiconductor wafer at the coordinate;
   obtaining, using the processor, a plurality of signed difference images, wherein each of the signed difference images is for one of the images at the coordinate;
   calculating, using the processor, a mean normalized value for the signed difference images;
   evaluating, using the processor, a consistency of a polarity in the signed difference images;
   applying, using the processor, a repeater threshold to the images;
   determining, using the processor, a number of defects that remain at the coordinate after the repeater threshold is applied; and
   setting the repeater threshold using the processor thereby providing a filter for nuisance.

2. The method of claim 1, further comprising performing a hot scan of the semiconductor wafer, wherein results from the hot scan are used for the repeater analysis.

3. The method of claim 1, wherein obtaining the difference image includes a single detection algorithm.

4. The method of claim 1, wherein obtaining the difference image includes a double detection algorithm.

5. The method of claim 4, wherein the signed difference image is used with a higher absolute repeater threshold per coordinate.

6. The method of claim 1, wherein the mean normalized value is calculated using an equation $$\frac{(\text{defect value} - \text{mean})}{\text{standard deviation}}.$$

7. The method of claim 6, wherein the repeater threshold is a maximum, and wherein the defect is a bright polarity defect.

8. The method of claim 6, wherein the repeater threshold is a minimum, and wherein the defect is a dark polarity defect.

9. The method of claim 1, further comprising sending instructions, using the processor, to image all of the reticles at a location of the repeater defect.

10. The method of claim 1, further comprising filtering, using the processor, the images using the repeater threshold that is set.

11. The method of claim 1, wherein calculating the repeater threshold includes evaluating a number of defects with bright polarity and a number of defects with dark polarity, and wherein a larger of the number of defects with bright polarity and the number of defects with dark polarity is used with the repeater threshold.

12. A non-transitory computer readable medium storing a program configured to instruct the processor to execute the method of claim 1.

13. A system comprising:
a broadband plasma tool that includes:
- a stage configured to hold a semiconductor wafer;
- a light source configured to direct light at the semiconductor wafer; and
- a detector configured to receive light reflected from the semiconductor wafer and generate an image;

a processor in electronic communication with the broadband plasma tool, wherein the processor is configured to:
- perform repeater analysis on a semiconductor wafer at a first threshold to remove non-repeater defects and identify repeater defects, wherein the repeater defects are located at a coordinate that is the same on each reticle;
- receive images on every reticle of the semiconductor wafer at the coordinate;
- obtain a plurality of signed difference images, wherein each of the signed difference images is for one of the images at the coordinate;
- calculate a mean normalized value for the signed difference images;
- evaluate a consistency of a polarity in the signed difference images;
- apply the repeater threshold to the images;
- determine a number of defects that remain at the coordinate after the threshold is applied; and
- set a repeater threshold thereby providing a filter for nuisance.

14. The system of claim 13, wherein the light source is one of a deep ultraviolet, ultraviolet, or variable illumination spectrum source.

15. The system of claim 13, wherein obtaining the difference image includes a single detection algorithm.

16. The system of claim 13, wherein obtaining the difference image includes a double detection algorithm, wherein the signed difference image is used with a higher absolute repeater threshold per coordinate.

17. The system of claim 13, wherein the mean normalized value is calculated using an equation $$\frac{(\text{defect value} - \text{mean})}{\text{standard deviation}},$$

wherein the repeater threshold is a maximum, and wherein the defect is a bright polarity defect.

18. The system of claim 13, wherein the mean normalized value is calculated using an equation $$\frac{(\text{defect value} - \text{mean})}{\text{standard deviation}},$$

wherein the repeater threshold is a minimum, and wherein the defect is a dark polarity defect.

19. The system of claim 13, wherein the processor is configured to send instructions to image all of the reticles at a location of the repeater defect.

20. The system of claim 13, wherein the processor is configured to filter the images using the repeater threshold that is set.

* * * * *